(12) United States Patent
Moritz

(10) Patent No.: US 9,539,394 B2
(45) Date of Patent: Jan. 10, 2017

(54) METHOD OF REDUCING FRICTION BETWEEN SYRINGE COMPONENTS

(75) Inventor: Michael P. Moritz, Media, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 976 days.

(21) Appl. No.: 13/446,900

(22) Filed: Apr. 13, 2012

(65) Prior Publication Data

US 2012/0260607 A1    Oct. 18, 2012

Related U.S. Application Data

(60) Provisional application No. 61/475,851, filed on Apr. 15, 2011.

(51) Int. Cl.
| | | |
|---|---|---|
| *A61M 5/28* | (2006.01) | |
| *B08B 3/10* | (2006.01) | |
| *B05D 5/08* | (2006.01) | |
| *A61M 5/31* | (2006.01) | |

(52) U.S. Cl.
CPC ............. *A61M 5/28* (2013.01); *A61M 5/3129* (2013.01); *B05D 5/08* (2013.01); *B08B 3/10* (2013.01); *A61M 2207/00* (2013.01); *Y10T 29/4984* (2015.01)

(58) Field of Classification Search
CPC ................ B08B 3/00; B08B 3/08; B08B 3/10; B08B 5/00; A61L 2/00; B05D 5/08; A61M 5/28; A61M 5/3129; A61M 2207/00; Y10T 29/4984
USPC .................................... 134/11, 19, 30, 31, 37
See application file for complete search history.

(56) References Cited

U.S. PATENT DOCUMENTS

| | | |
|---|---|---|
| 5,009,646 A | 4/1991 | Sudo et al. |
| 5,112,664 A | 5/1992 | Waterland, III et al. |
| 5,207,983 A | 5/1993 | Liebert et al. |
| 5,279,606 A | 1/1994 | Haber et al. |
| 6,030,694 A | 2/2000 | Dolan et al. |
| 6,090,081 A | 7/2000 | Sudo et al. |
| 6,331,351 B1 | 12/2001 | Waters et al. |
| 6,541,589 B1 | 4/2003 | Baillie |
| 7,111,848 B2 | 9/2006 | Tachikawa et al. |
| 7,521,010 B2 | 4/2009 | Kennedy et al. |
| 2009/0024095 A1* | 1/2009 | Frezza .......................... 604/222 |
| 2009/0093602 A1 | 4/2009 | Ford |
| 2011/0137263 A1* | 6/2011 | Ashmead et al. ............ 604/230 |

(Continued)

FOREIGN PATENT DOCUMENTS

| | | |
|---|---|---|
| EP | 0375778 B1 | 9/1990 |
| EP | 1317937 A1 | 6/2003 |

(Continued)

OTHER PUBLICATIONS

International Search Report and Written Opinion issued in PCT/US2010/054750, dated Feb. 17, 2011, 12 pages.

(Continued)

*Primary Examiner* — Saeed T Chaudhry

(57) ABSTRACT

A method of making a syringe assembly includes providing a first syringe component defining a first sliding surface that is substantially free of lubricant. The first sliding surface is contacted with water. The first sliding surface and the water in contact with the first sliding surface are heated at a temperature of at least 121° C. The first sliding surface is dried.

18 Claims, 3 Drawing Sheets

(56) References Cited

U.S. PATENT DOCUMENTS

2011/0282185 A1* 11/2011 Yanase .............. A61M 5/31513
600/420
2012/0251748 A1 10/2012 Ashmead et al.

FOREIGN PATENT DOCUMENTS

| GB | 0399336 A1 | 10/1933 |
|---|---|---|
| WO | WO9413469 A1 | 6/1994 |
| WO | WO9917816 A1 | 4/1999 |
| WO | WO0160534 A1 | 8/2001 |
| WO | WO03095552 A1 | 11/2003 |
| WO | WO2009082034 A1 | 7/2009 |
| WO | WO2011059823 A1 | 5/2011 |

OTHER PUBLICATIONS

International Search Report and Written Opinion issued in PCT/US2012/033616, mailed Sep. 27, 2012, 9 pages.

* cited by examiner

METHOD OF REDUCING FRICTION BETWEEN SYRINGE COMPONENTS

CROSS-REFERENCE TO RELATED APPLICATION

This application claims priority to Provisional Application No. 61/475,851, entitled "METHOD OF REDUCING FRICTION IN GLASS SYRINGE STOPPER," filed Apr. 15, 2011, which is incorporated herein by reference in its entirety for all purposes.

BACKGROUND

Syringes used for delivery of medicaments are principally constructed of a barrel and a stopper. The stopper is slidably fitted within the syringe barrel and may have a stopper rod affixed to it for actuation of the syringe and delivery of medicament. The stopper is generally constructed of an elastomer, with silicone oil applied. The silicone oil is applied to the stopper or barrel to reduce sliding friction between the stopper and barrel and to improve the seal between them, which can be helpful in ensuring a full dose is administered. Ease of sliding can be important for proper operation of pens and so-called auto injecting syringes. The oil helps prevent jamming of such devices, which can otherwise lead to trauma at the site of injection. The improved sealing provided by silicone oil can also help ensure no foreign contaminants, such as bacteria, enter the syringe.

Recently there has developed a trend favoring pre-filled syringes which function to both store and deliver medicaments. Such pre-filled syringes may offer cost savings to the pharmaceutical industry and may improve safety, convenience and efficacy of medicament delivery. Biopharmaceuticals are an important class of pharmaceuticals that may increase the use of pre-filled syringes and related devices (pens, auto injectors and the like). Such biopharmaceuticals may include insulin, vaccines, antibodies, blood products, hormones, cytokines, and the like. As more pharmaceuticals and particularly biopharmaceuticals utilize delivery in pre-filled syringes and similar devices, the challenges of conventional syringe technology multiply.

Several aspects of traditional syringe construction present a challenge for their use as pre-filled syringes. The use of silicone oil is a concern, because the oil may degrade the medicament and because a small amount of silicone may be injected with it. The oil is of particular concern with regard to biopharmaceuticals because it may cause aggregation of certain proteins.

Another issue that arises in pre-filled syringes is that the elastomer of the stopper may contain leachable and extractable contaminants. These may also contaminate the medicament upon long term storage in syringes. Trace amounts of residual monomer or plasticizer or other impurities from the stopper can adversely affect the therapeutic function or can have an adverse impact on the patient once injected.

Among the many other considerations affecting pre-filled syringe devices and similar devices and their components are the need to be sterilized, stability with transport and storage for up to a few years, optical clarity, the need to integrate into existing filling equipment (including the durability requirements for stopper cleaning and insertion into the syringe barrel), leachables and extractables of all components of the syringe, and the need to maintain sterility from filling through administering of the contents, and finally user preferences and ergonomic considerations. For a variety of considerations the pre-filled syringe market uses both glass and plastic barrels.

Friction between stopper materials and syringe barrels can be significant. As described above, lubricants such as silicone oil are problematic. There is a need to reduce friction between stopper and barrel without the use of oils or other lubricants that have undesirable effects.

SUMMARY

Some aspects relate to a method of reducing sliding friction between glass and a stopper material. The method includes exposing glass to an aqueous solution at high temperature. For example, the glass is optionally contacted with water for injection (WFI) water and placed in an autoclave set at a temperature at or above 120° C. Following the autoclave process, the glass is dried at about 90° C. Friction between a stopper material and glass are thereby reduced significantly. In another aspect, the method may include rinsing the glass, for example with an organic solvent.

Other aspects relate to a method of making a syringe assembly including providing a first syringe component defining a first sliding surface that is substantially free of lubricant. The first sliding surface is contacted with water, the first sliding surface and the water in contact with the first sliding surface are heated at a temperature of at least 121° C., and the first sliding surface is dried.

Still other aspects relate to a component of a syringe assembly that is prepared for sliding engagement with a second, complementary component of the syringe assembly by a process including contacting the first sliding surface with WFI water. Saturated steam is applied to heat the first sliding surface and the WFI water in contact with the first sliding surface and the first sliding surfaced is dried.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
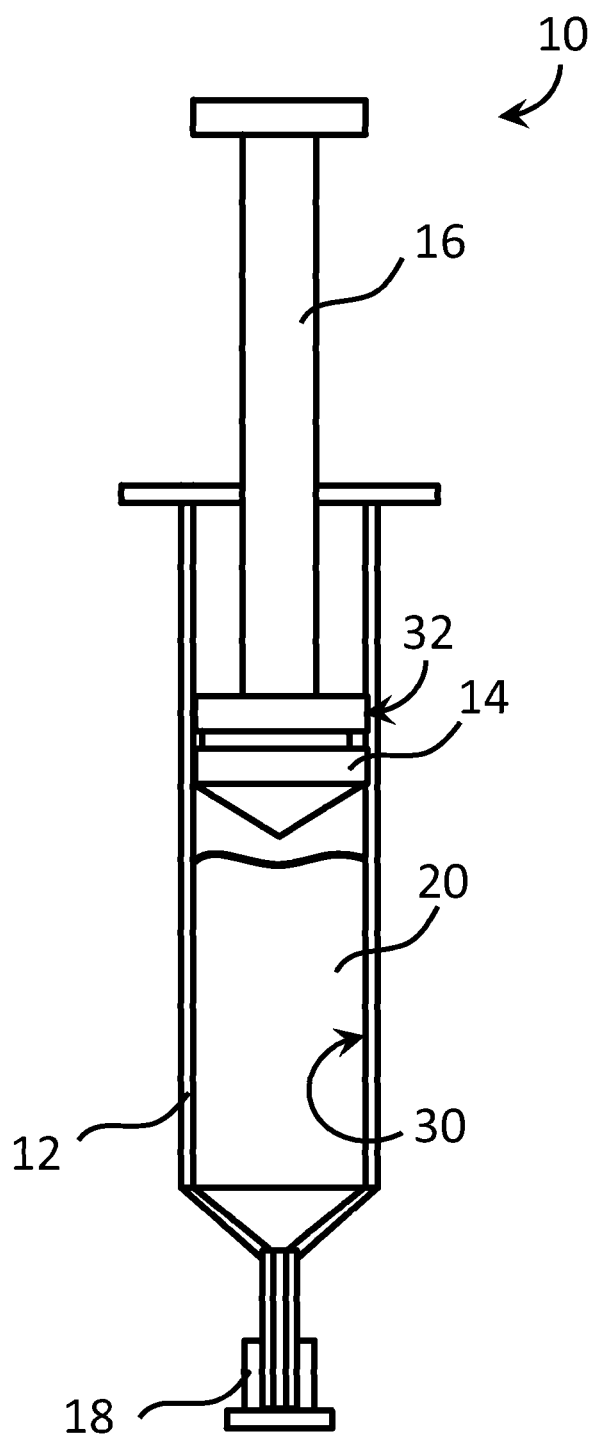
FIG. 1 is a schematic view of a syringe assembly prepared according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments described herein address reducing sliding friction between complementary sliding components in syringe assemblies, such as friction reduction between a first, softer component and a second, more rigid component of a syringe assembly. For example, some embodiments relate to reducing friction between a syringe stopper and a barrel, between a syringe tip cap and a barrel, or between a syringe valve body and valve plug, or other complementary syringe components. In some embodiments, the first component (e.g., a stopper) includes an elastomeric material, such as butyl rubber, and the second component (e.g., a syringe barrel) includes a ceramic material, such as borosilicate glass. While various embodiments are described in association with syringe assembly applications, a variety of applications where reduced friction is sought are contemplated.

FIG. 1 is a schematic view of a syringe assembly 10, according to some embodiments. As shown, the syringe assembly 10 includes a syringe barrel 12, a stopper 14 that forms a complementary fit with the syringe barrel 12, a plunger rod 16, a tip cap or needle shield 18, and, in the case of a pre-filled embodiment, a liquid 20, such as a medicament, for dispensing from the syringe assembly 10. As shown, the syringe barrel 12 and the stopper 14 are first and second complementary syringe components that are slidably engaged with one another, the stopper 14 forming a slidable seal within the syringe barrel 12. Although the syringe barrel 12 and the stopper are slidably engaged in a linear relationship, it should be understood that other sliding relationships (e.g., rotational sliding between a valve body and a valve plug) are contemplated.

As shown, the syringe barrel 12 defines a bore or inner surface 30, also described as a sliding surface. The syringe barrel 12 is formed of a suitable material, such as suitable ceramic, polymeric, and metal materials. In some embodiments, the syringe barrel 12 includes a substantially rigid or hard material, such as a glass material. Although any of a variety of glass compositions are contemplated, according to the examples that follow borosilicate glass has been shown to be an effective material in association with friction-reduction methods according to some embodiments.

As indicated in FIG. 1, the stopper 14 defines an outer surface 32 for slidably engaging the inner surface 30 of the syringe barrel 12. In some embodiments, the stopper 14 includes a softer material than the syringe barrel 12. For example, the stopper 14 is optionally constructed with one or more barrier films applied to an elastomeric core, where the barrier film(s) define the outer surface 32 of the stopper 14. The elastomeric core can be formed of a variety of elastomeric materials, including: Butyl Rubber, Silicon, materials sold under the trade name "VITON", and the like. The barrier film or films optionally include expanded fluoropolymer films and, such as expanded polytetrafluoroethylene films. Barrier films based on expanded PTFE help provide for thin and strong barrier layers to leachables and extractables. Some examples of suitable stopper designs utilizing expanded PTFE and elastomeric materials are described in U.S. application Ser. No. 12/915,850, "SYRINGE STOPPER" by Ashmead et al., filed Oct. 29, 2010, the entire contents of which are incorporated herein by reference for all purposes.

In some embodiment methods of reducing friction between the stopper 14 and the syringe barrel 12 of the syringe assembly 10, the syringe barrel 12 is filled with WFI water and sealed to prevent leakage. A cap, a second stopper, or other sealing member (not shown) different than the stopper 14 is optionally utilized to seal the WFI water within the syringe barrel 12. In other embodiments, the assembly 10, including the stopper 14 is filled with WFI water. The WFI water filled syringe barrel 12 is exposed to a source of heat, such as saturated steam. For example, the WFI water filled syringe barrel 12 may be placed in an autoclave with the temperature set at 121° C. or above. The saturated steam will heat the WFI water and the syringe barrel 12. The WFI water is removed and the syringe barrel 12 is dried. Following drying, the syringe barrel 12 is ready for use. Syringe assemblies with syringe barrels thus prepared display lower frictional forces between the syringe barrel 12 and the stopper 14.

In some embodiments, the syringe barrel 12 is rinsed with an organic solvent after the syringe barrel 12 and associated WFI water have been heated with steam. For example, a Hexane solvent may be used to rinse the syringe barrel 12. After the rinsing step, the syringe barrel 12 is dried. Drying may be conducted at room temperature (RT) or at elevated temperatures (e.g., at about 90° C. or greater, from about 70° C. to about 110° C., other at other temperature(s) as desired). The following examples are illustrative of methods of preparing a syringe assembly 10 with reduced friction according to some embodiments. While various methods of reducing friction between the syringe barrel 12 and the stopper 14 have been described, it should be understood that in other implementations similar methodology is applied to reduce friction between alternative or additional components of the syringe assembly 10, such as between the syringe barrel 12 and the tip cap 18, for example.

EXAMPLES

A syringe stopper was constructed in the following manner: A layer of FEP about 0.5 mils in thickness (FEP 100, DuPont) was laminated to a layer of densified expanded PTFE film [thickness: 1 mil; tensile strength: 13.85 ksi (longitudinal), 13.9 ksi (transverse); modulus: 19.8 ksi (longitudinal), 20.7 ksi (transverse); strain to break: 425% (longitudinal), 425% (transverse)]. The two layers were stacked on top of each other in a pin frame and heating to 380° C. in an oven for 15 minutes. A layer of porous expanded PTFE [thickness: 27.5 micrometers, matrix tensile strength: 66.8 MPa (longitudinal), 75.8 MPa (transverse), strain to break: 131% (longitudinal), 91% (transverse), bubble point: 22.6 psi] was placed on the densified ePTFE-FEP laminate such that the porous expanded PTFE layer faced the FEP layer in the laminate. These three layers were placed between two smooth metal plates, the plates were clamped to a clamping pressure of about 1 psi. The plates were then placed in an oven at 305° C. for 15 minutes. The resulting three layer composite material (densified ePTFE-FEP-porous ePTFE) was then cooled to about 40° C.

This composite material was then thermoformed using heat and vacuum to create a pre-form. The pre-form was constructed by heating the composite to a sufficiently high temperature and then drawing the composite over a male plug using differential pressure. The composite material was loaded into the thermoforming apparatus such that the densified ePTFE layer faced the plug. The composite was heated using a hot air gun (Steinel HG2310) with air exit temperature of 380° C. by placing the gun about 5 mm away from the surface of the composite. After 5 seconds, the film was subjected to a vacuum of −85 kPa. The composite was continued to be heated for another 15 seconds and cooled to about 40° C. under vacuum.

The resulting pre-form sample was then inverted and then placed into a rubber molding cavity charged with 3.5 grams of elastomer (50 Durometer halobutyl rubber), and the stopper was formed by compression molding. The mold was built to geometry specified for 1 mL "long" plunger per the ISO standard IS011040-5:2001(E), with an additional 2% shrinkage factor incorporated.

The cavity was loaded in a press with both platens preheated to 120° C. The platens were closed to 55,500 lbs (about 8700 psi total internal pressure). The platens were then heated at 180° C. for 5 minutes and then cooled under pressure to 40° C. The pressure was released and the stopper was ejected. The resulting stopper was washed using a detergent and triple rinsed with de-ionized water. Stopper samples were then cut from the release sheet using a razor blade. They were subjected to two 30 minute cycles in an autoclave at 121° C.

Figure 2:
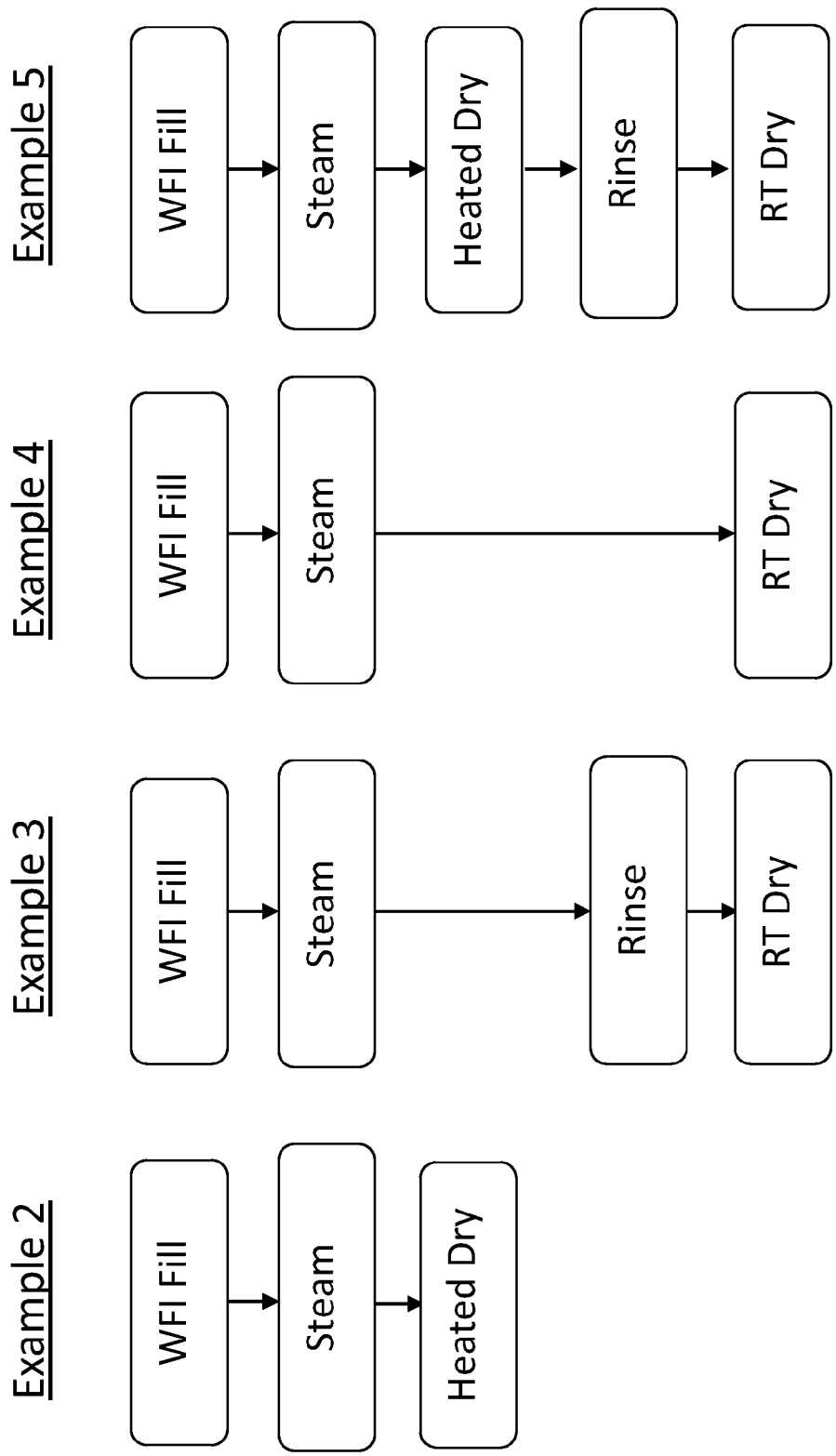
FIG. 2 provides flow charts illustrating the methods of Examples 2 to 5.
Figure 3:
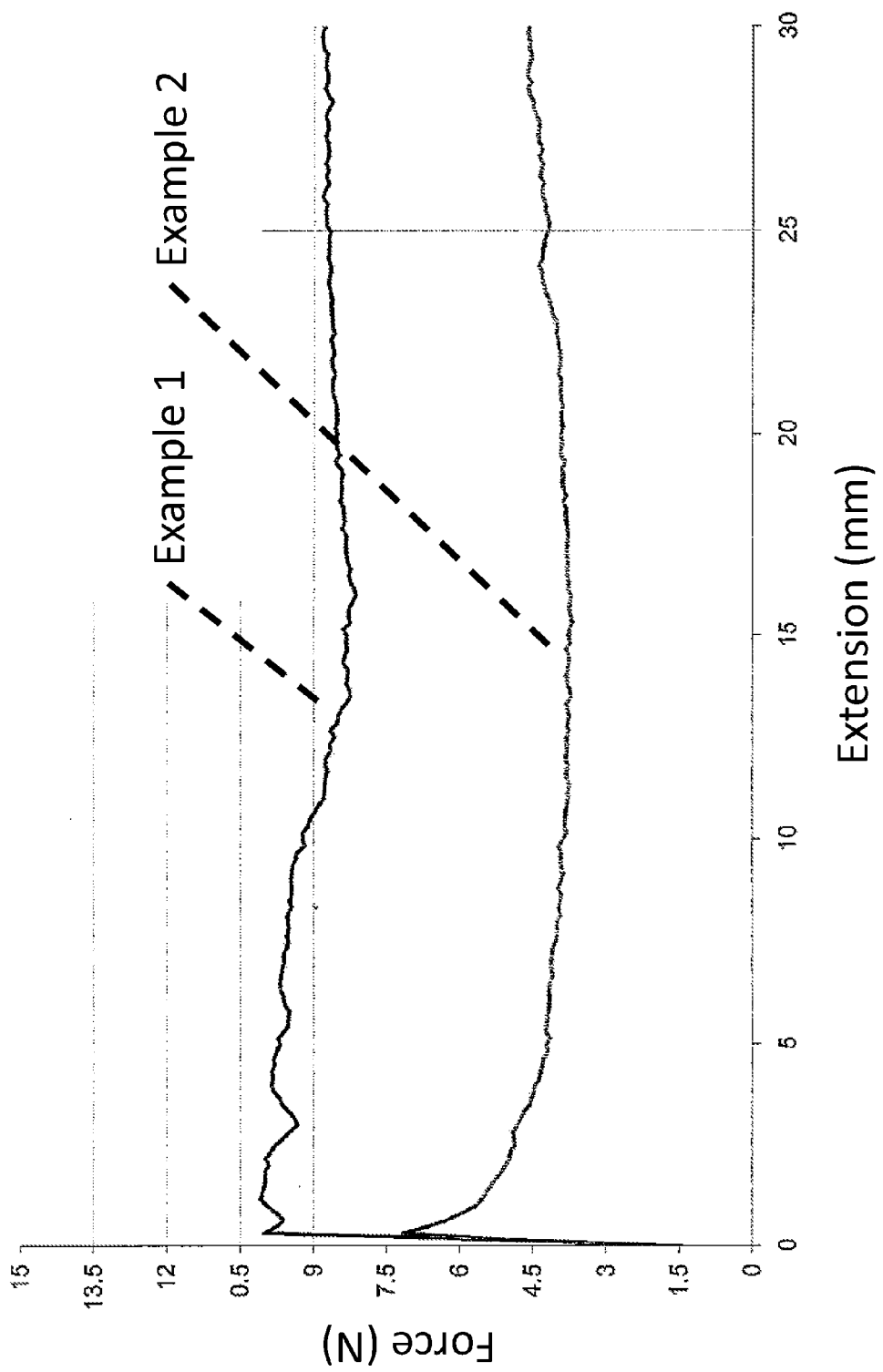
FIG. 3 is a chart reflecting functional forces of Comparative Example 1 and Example 2.

As constructed, the stoppers were used as in the following examples, which reflect the improved sliding friction of the present invention when compared to that of the comparative example. A new stopper was used in each of the examples. FIG. 2 provides flow charts illustrating the methods of Examples 2 to 5.

Comparative Example 1

As Delivered

A borosilicate glass syringe (1 mL Long Schott forma 3 s with a staked needle) was obtained. The syringe was obtained without silicone oil applied. A stopper constructed as described above was inserted into the barrel of the syringe and the Dynamic force was measured. Results are reported in Table I.

Example 2

A syringe according to the inventive method was constructed in the following manner: A glass syringe free of silicone oil identical to that used in Example 1 was filled with WFI grade water and placed in an autoclave (121° C. for 1 hr), the glass syringe was then dried at 90° C. for 60 minutes and allowed to cool overnight. The stopper was then inserted into the syringe and the dynamic force was measured to be 4.7N. Results are reported in Table I.

Example 3

A glass syringe free of silicone oil identical to that of Example 1 was filled with WFI grade water and placed in an autoclave (121° C. for 1 hr), the glass syringe was then removed from the autoclave, rinsed with hexane and dried at room temperature overnight in a laboratory hood. Another stopper was then inserted into this syringe and the dynamic force was measured to be 1.1N. Results are reported in Table I.

Example 4

A glass syringe free of silicone oil identical to that of Comparative Example 1 was filled with WFI grade water and placed in an autoclave (121° C. for 1 hr), the glass syringe was then removed from the autoclave and dried at room temperature overnight in a laboratory hood. The stopper was then inserted into this syringe and the dynamic force was measured to be 5.9N. Results are reported in Table I.

Example 5

A glass syringe free of silicone oil identical to that of Comparative Example 1 was filled with WFI grade water and placed in an autoclave (121° C. for 1 hr), the glass syringe was then removed from the autoclave and then dried at 90° C. for 60 minutes. The syringe was then rinsed with hexane and allowed to dry overnight in a laboratory hood. The stopper was then inserted into this syringe and the dynamic force was measured to be 4.4 N. Results are reported in Table I.

Example 6

The syringe of Example 2 was tested per the dye ingress test in USP <381> to evaluate the seal between the inside of the syringe barrel and the stopper from Example 1. No significant dye ingress was observed.

TABLE 1

|  | Static Force (N) | Dynamic Force (N) |
| --- | --- | --- |
| Comparative Example 1 | 10.1 | 8.5 |
| Example 2 | 7.0 | 4.7 |
| Example 3 | 7.3 | 1.1 |
| Example 4 | 8.5 | 5.9 |
| Example 5 | 6.4 | 4.4 |

As shown in Table 1, subjecting the glass syringe to the treatments described in Examples 2 through 5 lower the dynamic and static force of the stopper.

Test Methods:

Static and Dynamic Force Test

The test was performed as specified by I.S. EN ISO 7886-1:1998 Annex G, with the following exceptions: i) Syringe is mounted so that nozzle is pointing down, ii) No liquid was expelled; only air was expelled, and iii) Forces resulting from travel from the total graduated capacity position to 20 mm from that point were recorded. Static force is defined as the value at the first inflection point in the force versus displacement graph. Dynamic force is the value after the inflection point during travel.

Tensile, Modulus, Strain to Break

Materials were evaluated for tensile strength, modulus and strain to break according to ATM D882-10 using 0.25 inch by 3 inch samples and a cross head rate of 20 inches/min and one inch gauge length.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of reducing friction in a glass syringe comprising: treating a glass syringe barrel, including:
    filling said glass syringe barrel with water for injection (WFI),
    applying saturated steam to said glass syringe barrel at a temperature of at least 121° C. to heat the glass syringe barrel and the WFI,
    removing the WFI from the barrel, and
    drying the inside of the glass syringe barrel at room temperature, wherein the dried glass surface provides reduced friction.

2. The method of claim 1 wherein the drying step is performed at above 90° C.

3. The method of claim 1 further comprising:
   rinsing the glass syringe barrel with a solvent following the drying step; and
   drying the glass syringe barrel at or above 90° C. following the rinsing step.

4. The method of claim 1 wherein the glass syringe barrel comprises borosilicate glass.

5. The method of claim 1 further comprising the step of rinsing the glass syringe barrel with an organic solvent.

6. The method of claim 5 wherein the rinsing step is performed prior to the drying step.

7. The method of claim 5 wherein the organic solvent is hexane.

8. The method of claim 1 wherein the glass syringe barrel is substantially free of lubricant prior to filling the glass syringe barrel with WFI.

9. The method of claim 1 wherein the glass syringe barrel is substantially free of silicone oil prior to filling the glass syringe barrel with said WFI.

10. A method for reducing friction in a syringe barrel, said method comprising:
    providing a syringe barrel defining a first sliding surface that is substantially free of lubricant; and
    treating the first sliding surface by
    (a) contacting the first sliding surface with water for injection (WFI);
    (b) heating the first sliding surface and the WFI in contact with the first sliding surface at a temperature of at least 121° C.;
    (c) removing the WFI from the first sliding surface; and
    (d) drying the first sliding surface wherein following treating steps (a) to (d), the friction of the first sliding surface is reduced.

11. The method of claim 10 wherein heating the first sliding surface and the WFI includes applying saturated steam at a temperature of at least 121° C. to heat the first sliding surface and the WFI.

12. The method of claim 10 wherein the first sliding surface comprises a glass material.

13. The method of claim 10 further comprising:
    providing a stopper defining a second sliding surface configured for sliding engagement with the first sliding surface; and
    slidably contacting the first sliding surface with the second sliding surface to form a syringe assembly.

14. The method of claim 13 wherein the stopper is softer than the first syringe component.

15. The method of claim 13, wherein the first sliding surface is slidably contacted with the second sliding surface after applying saturated steam to heat the first sliding surface and the WFI in contact with the first sliding surface.

16. The method of claim 15 wherein the syringe barrel is substantially free of silicone oil prior to filling the syringe barrel with said WFI.

17. The method of claim 13, further comprising filling the syringe barrel with a medicament and storing the syringe assembly.

18. The method of claim 10, further comprising at least one of:
    drying the first sliding surface at room temperature after applying saturated steam,
    drying the first sliding surface at or above 90° C. after applying saturated steam, and
    rinsing the first sliding surface with an organic solvent after applying saturated steam.

* * * * *